United States Patent
Parisi et al.

(10) Patent No.: US 10,166,121 B2
(45) Date of Patent: Jan. 1, 2019

(54) BONE PRESERVING INTRAOPERATIVE DOWNSIZING SYSTEM FOR ORTHOPAEDIC IMPLANTS

(71) Applicant: Zimmer, Inc., Warsaw, IN (US)

(72) Inventors: Raymond C. Parisi, Wakarusa, IN (US); Charles A. Baldridge, Pierceton, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/891,558

(22) Filed: Feb. 8, 2018

(65) Prior Publication Data

US 2018/0228625 A1 Aug. 16, 2018

Related U.S. Application Data

(60) Division of application No. 14/660,154, filed on Mar. 17, 2015, now Pat. No. 9,931,228, which is a
(Continued)

(51) Int. Cl.
*A61B 17/15* (2006.01)
*A61F 2/46* (2006.01)
(Continued)

(52) U.S. Cl.
CPC .......... *A61F 2/4684* (2013.01); *A61B 17/155* (2013.01); *A61F 2/3859* (2013.01);
(Continued)

(58) Field of Classification Search
CPC ..... A61B 17/15; A61B 17/154; A61B 17/155; A61F 2/4684; A61F 2002/30616
(Continued)

(56) References Cited

U.S. PATENT DOCUMENTS 5,129,909 A * 7/1992 Sutherland ........... A61B 17/155
606/53
5,226,915 A * 7/1993 Bertin ................. A61F 2/30734
623/20.15
(Continued)

FOREIGN PATENT DOCUMENTS

WO WO 2004016204 A1 * 2/2004 ........... A61B 17/155
WO WO-2004016204 A1 2/2004
(Continued)

OTHER PUBLICATIONS

"U.S. Appl. No. 13/229,100, Non Final Office Action dated Jun. 5, 2014", 16 pgs.
(Continued)

*Primary Examiner* — Eric S Gibson
(74) *Attorney, Agent, or Firm* — Schwegman Lundberg & Woessner, P.A.

(57) ABSTRACT

An orthopedic implant system includes a set of provisional orthopedic implants having different implant sizes, in which each provisional implant facilitates an intraoperative selection of the next-smallest implant size without removing the provisional implant from the bone. All of the implant sizes share a common sagittal configuration of distal and anterior bone contacting surfaces, but have variable sagittal configurations only in the posterior bone contacting surfaces. Thus, where a relatively larger femoral provisional component is mounted to a femur, changing to a smaller provisional component (i.e., "downsizing") can be accomplished by recutting only two of five original femoral cuts. Cut slots provided in each provisional implant are sized and positioned to correspond to the posterior bone contacting surface geometry of the next-smallest provisional implant size. Thus, the cut slots in a mounted, relatively larger implant
(Continued)

can be used to further resect posterior femoral surfaces to accept the next smallest implant component size.

14 Claims, 12 Drawing Sheets

Related U.S. Application Data continuation of application No. 13/229,100, filed on Sep. 9, 2011, now Pat. No. 9,011,453.

(60) Provisional application No. 61/381,802, filed on Sep. 10, 2010.

(51) Int. Cl.
*A61F 2/38* (2006.01)
*A61F 2/30* (2006.01)

(52) U.S. Cl.
CPC .......... *A61F 2002/30616* (2013.01); *A61F 2002/30892* (2013.01)

(58) Field of Classification Search
USPC .............. 606/86 R–89 R; 623/20.14–20.35
See application file for complete search history.

(56) References Cited

U.S. PATENT DOCUMENTS

| | | | | |
|---|---|---|---|---|
| 5,258,032 A * | 11/1993 | Bertin | ............... | A61B 17/155 606/88 |
| 5,417,693 A * | 5/1995 | Sowden | ............ | A61B 17/1659 269/234 |
| 5,458,645 A * | 10/1995 | Bertin | ............... | A61B 17/155 128/898 |
| 5,474,559 A | 12/1995 | Bertin et al. | | |
| 5,702,460 A * | 12/1997 | Carls | ............... | A61B 17/155 606/79 |
| 5,716,361 A * | 2/1998 | Masini | ............... | A61B 17/154 606/82 |
| 5,743,915 A | 4/1998 | Bertin et al. | | |
| 5,769,855 A | 6/1998 | Bertin et al. | | |
| 5,776,201 A * | 7/1998 | Colleran | ............... | A61F 2/4684 606/88 |
| 5,853,415 A | 12/1998 | Bertin et al. | | |
| 5,860,981 A | 1/1999 | Bertin et al. | | |
| 5,879,393 A * | 3/1999 | Whiteside | ............ | A61B 17/155 606/88 |
| 5,885,296 A | 3/1999 | Masini | | |
| 5,916,220 A | 6/1999 | Masini | | |
| 5,947,973 A * | 9/1999 | Masini | ............... | A61B 17/154 606/87 |
| 5,961,523 A * | 10/1999 | Masini | ............... | A61B 17/154 606/82 |
| 6,077,269 A | 6/2000 | Masini | | |
| 6,080,196 A * | 6/2000 | Bertin | ............... | A61B 17/155 606/102 |
| 6,187,010 B1 * | 2/2001 | Masini | ............... | A61B 17/154 606/82 |
| 6,488,687 B1 | 12/2002 | Masini | | |
| 6,500,179 B1 * | 12/2002 | Masini | ............... | A61B 17/155 606/102 |
| 6,503,254 B2 | 1/2003 | Masini | ............... | A61B 17/154 606/86 R |
| 6,575,980 B1 * | 6/2003 | Robie | ............... | A61B 17/155 606/82 |
| 6,589,283 B1 * | 7/2003 | Metzger | ............... | A61F 2/3886 606/88 |
| 6,673,077 B1 * | 1/2004 | Katz | ............... | A61B 17/154 606/102 |
| 6,827,739 B2 * | 12/2004 | Griner | ............... | A61B 17/155 623/16.11 |
| 6,916,324 B2 * | 7/2005 | Sanford | ............... | A61B 17/155 606/87 |
| 6,962,593 B2 * | 11/2005 | Sanford | ............... | A61B 17/155 606/88 |
| RE39,301 E * | 9/2006 | Bertin | ............... | A61B 17/155 128/898 |
| 7,128,745 B2 * | 10/2006 | Masini | ............... | A61B 17/154 606/88 |
| 7,172,597 B2 * | 2/2007 | Sanford | ............... | A61B 17/155 606/88 |
| 7,306,609 B2 * | 12/2007 | Schmotzer | ............... | A61B 17/155 606/88 |
| 7,419,491 B2 | 9/2008 | Masini | | |
| 7,572,262 B1 * | 8/2009 | Hoeppner | ............... | A61B 17/155 606/87 |
| 7,666,187 B2 * | 2/2010 | Axelson, Jr. | ............... | A61B 17/155 606/88 |
| 7,780,671 B2 * | 8/2010 | Berger | ............... | A61B 17/157 606/79 |
| 7,878,989 B2 * | 2/2011 | McMinn | ............... | A61F 2/3859 600/550 |
| 7,963,968 B2 * | 6/2011 | Dees, Jr. | ............... | A61B 17/1675 606/88 |
| 8,002,840 B2 * | 8/2011 | Aram | ............... | A61B 17/1764 623/20.15 |
| 8,038,681 B2 * | 10/2011 | Koenemann | ............... | A61B 17/155 606/88 |
| 8,118,811 B2 * | 2/2012 | Coon | ............... | A61B 17/155 606/86 R |
| 8,246,626 B2 * | 8/2012 | Cuckler | ............... | A61B 17/1764 606/88 |
| 8,337,501 B2 * | 12/2012 | Fitz | ............... | A61B 17/1767 606/86 R |
| 8,337,507 B2 * | 12/2012 | Lang | ............... | G06K 9/00 606/102 |
| 8,403,935 B2 * | 3/2013 | Gross | ............... | A61B 17/155 606/87 |
| 8,409,210 B2 * | 4/2013 | Bhatnagar | ............... | A61F 2/38 606/88 |
| 8,551,102 B2 * | 10/2013 | Fitz | ............... | A61B 5/4528 606/88 |
| 8,551,103 B2 * | 10/2013 | Fitz | ............... | A61B 5/4528 606/88 |
| 8,551,179 B2 * | 10/2013 | Jones | ............... | A61F 2/3859 623/20.35 |
| 8,556,907 B2 * | 10/2013 | Fitz | ............... | A61B 5/4528 606/87 |
| 9,011,453 B2 * | 4/2015 | Parisi | ............... | A61B 17/155 606/88 |
| 9,931,228 B2 * | 4/2018 | Parisi | ............... | A61B 17/155 |
| 2003/0225458 A1 * | 12/2003 | Donkers | ............... | A61F 2/3859 623/20.15 |
| 2004/0039450 A1 * | 2/2004 | Griner | ............... | A61B 17/155 623/20.31 |
| 2004/0078043 A1 * | 4/2004 | Masini | ............... | A61B 17/154 606/88 |
| 2004/0153087 A1 * | 8/2004 | Sanford | ............... | A61B 17/155 606/88 |
| 2006/0122617 A1 * | 6/2006 | Lavallee | ............... | A61B 17/155 606/87 |
| 2006/0167460 A1 | 7/2006 | Pinczewski et al. | | |
| 2006/0173463 A1 * | 8/2006 | Dees, Jr. | ............... | A61B 17/1675 606/88 |
| 2006/0195113 A1 * | 8/2006 | Masini | ............... | A61B 17/154 606/87 |
| 2006/0265078 A1 * | 11/2006 | McMinn | ............... | A61B 17/155 623/20.14 |
| 2007/0123992 A1 | 5/2007 | Sanford | | |
| 2007/0233141 A1 * | 10/2007 | Park | ............... | A61B 17/155 606/88 |
| 2008/0091209 A1 * | 4/2008 | Schmotzer | ............... | A61B 17/155 606/88 |
| 2008/0140212 A1 * | 6/2008 | Metzger | ............... | A61F 2/3886 623/20.31 |
| 2009/0088762 A1 * | 4/2009 | Koenemann | ............... | A61B 17/155 606/88 |

(56) References Cited

U.S. PATENT DOCUMENTS

| | | | | |
|---|---|---|---|---|
| 2009/0093816 A1* | 4/2009 | Roose | A61B 17/155 | 606/87 |
| 2009/0265011 A1* | 10/2009 | Mandell | A61B 17/155 | 623/20.15 |
| 2009/0265013 A1* | 10/2009 | Mandell | A61F 2/30734 | 623/20.21 |
| 2011/0213374 A1* | 9/2011 | Fitz | A61B 17/154 | 606/87 |
| 2011/0218539 A1* | 9/2011 | Fitz | A61B 17/154 | 606/87 |
| 2011/0245835 A1* | 10/2011 | Dodds | A61B 17/155 | 606/87 |
| 2012/0078263 A1* | 3/2012 | Parisi | A61B 17/155 | 606/89 |
| 2015/0182352 A1* | 7/2015 | Parisi | A61B 17/155 | 623/20.15 |

FOREIGN PATENT DOCUMENTS

| | | | | |
|---|---|---|---|---|
| WO | WO 2008054389 A1 * | 5/2008 | | A61B 17/155 |
| WO | WO-2008054389 A1 | 5/2008 | | |

OTHER PUBLICATIONS

"U.S. Appl. No. 13/229,100, Notice of Allowance dated Dec. 22, 2014", 8 pgs.

"U.S. Appl. No. 13/229,100, Preliminary Amendment filed Dec. 14, 2010", 3 pgs.

"U.S. Appl. No. 13/229,100, Response filed Feb. 12, 2014 to Restriction requirement dated Jan. 14, 2014", 10 pgs.

"U.S. Appl. No. 13/229,100, Restriction Requirement dated Jan. 14, 2014", 7 pgs.

"U.S. Appl. No. 13/299,100, Response filed Nov. 4, 2014 to Non-Final Office Action dated Jun. 5, 2014", 20 pgs.

"U.S. Appl. No. 14/660,154, Non Final Office Action dated Jul. 21, 2017", 17 pgs.

"U.S. Appl. No. 14/660,154, Notice of Allowance dated Nov. 22, 2017", 5 pgs.

"U.S. Appl. No. 14/660,154, Preliminary Amendment filed Mar. 18, 2015", 8 pgs.

"U.S. Appl. No. 14/660,154, Response filed Oct. 19, 2017 to Non Final Office Action dated Jul. 21, 2017", 18 pgs.

"Zimmer MIS Multi-Reference 4-in-1 Femoral Instrumentation Surgical Technique", Zimmer, Inc., (2003, 2008, 2009), 48 pgs.

* cited by examiner

BONE PRESERVING INTRAOPERATIVE DOWNSIZING SYSTEM FOR ORTHOPAEDIC IMPLANTS

CROSS-REFERENCE TO RELATED APPLICATIONS

This application is a division of U.S. patent application Ser. No. 14/660,154, filed Mar. 17, 2015, which is a continuation of U.S. patent application Ser. No. 13/229,100, filed on Sep. 9, 2011, now issued as U.S. Pat. No. 9,011,453, which claims the benefit under Title 35, U.S.C. § 119(e) of U.S. Provisional Patent Application Ser. No. 61/381,802, filed on Sep. 10, 2010 and entitled PROVISIONAL ORTHOPAEDIC IMPLANT WITH INTEGRAL CUTTING GUIDE, the benefit of priority of each of which is claimed hereby, and each of which are incorporated by reference herein in its entirety.

BACKGROUND

1. Technical Field

The present disclosure relates to orthopaedic prostheses and, more particularly, to provisional orthopaedic prosthetic components that can be used to facilitate the intraoperative selection of one of a set of differently configured permanent prosthetic components.

2. Description of the Related Art

Orthopaedic prostheses are commonly utilized to repair and/or replace damaged bone and tissue in the human body. For example, a knee prosthesis may include a femoral component which replaces the articular surface of one or both of the natural femoral condyles. Frequently, the femoral component articulates with a tibial component attached to the proximal end of the patient's tibia, so that the knee prosthesis completely replaces the articular surfaces of the natural femur and tibia.

During a conventional surgical procedure to implant a knee prosthesis, a provisional femoral component and a provisional tibial component may be placed on a resected distal femur and resected proximal tibia, respectively. The provisional components are used to ensure proper fit of the prosthetic components upon their respective resected surfaces prior to implantation of the permanent component, and may also be used to assess the kinematic profile (e.g., range of motion, ligament/tendon tension, etc.) expected of the knee prosthesis after implantation. To this end, provisional components are typically provided in a range of sizes and/or configurations, with each size substantially identical to a corresponding permanent prosthetic component. In some prosthesis systems, a wide range of sizes is available with a relatively small size difference between adjacent sizes. This "fine resolution" in the range of sizes seeks to ensure a proper fit of the implant on the bone, and to optimize the interaction between the implant and adjacent components and anatomic structures. Moreover, providing many implant sizes facilitates knee replacement surgery for the widest possible variety of patient anatomies.

In surgery, instrumentation for an initial resection of the bone is typically chosen based upon known characteristics of the preoperative bone, such as may be ascertained by preoperative imaging, intraoperative measurements, and the like. Alternatively, the instrumentation may be chosen intraoperatively after the bone is exposed, based on a surgeon's assessment of the most desirable resection profile for a given patient. A first provisional component corresponding to the particular size and geometry of the initial resection is then selected, and is attached to the femur and/or tibia after resections appropriate to the chosen trial component sizes are completed.

The fit of the provisional component is then evaluated, and the knee prosthesis may be articulated through a range of motion to assess kinematic characteristics of the new prosthesis, such as ligament tension throughout the range of motion. If the kinematic characteristics are undesirable, or some parameter of prosthesis fit is incorrect, a differently sized tibial and/or femoral component may be selected. In some instances, the differently sized component requires recutting or otherwise modifying the distal femur after the first provisional component is removed. Substantial design efforts have been focused on providing instrument guides suitable for performing such additional cuts or modifications, such as instrument guides including pins, screws or other attachment mechanisms for connecting the guides to the previously resected distal femur.

Once the femur has been recut to accept the new size of provisional component, the new component is attached to the femur and the provisional knee prosthesis is again articulated throughout a range of motion to assess kinematic characteristics and other fit characteristics. If undesirable kinematic and/or fit characteristics persist, additional prosthesis sizes may be chosen—and further resection of the distal femur to accommodate the differently sized provisionals performed as needed—until an acceptable prosthesis is found.

SUMMARY

The present disclosure provides an orthopaedic implant system including a set of provisional orthopaedic implants having different implant sizes, in which each provisional implant facilitates an intraoperative selection of the next-smallest implant size without removing the provisional implant from the bone. All of the implant sizes share a common sagittal configuration of distal and anterior bone contacting surfaces, but have variable sagittal configurations only in the posterior bone contacting surfaces. Thus, where a relatively larger femoral provisional component is mounted to a femur, changing to a smaller provisional component (i.e., "downsizing") can be accomplished by recutting only two of five original femoral cuts. Cut slots provided in each provisional implant are sized and positioned to correspond to the posterior bone contacting surface geometry of the next-smallest provisional implant size. Thus, the cut slots in a mounted, relatively larger implant can be used to further resect posterior femoral surfaces to accept the next smallest implant component size.

The provisional implants have articular and bone-contacting geometry identical to corresponding permanent femoral implants, allowing the provisional implants to be used to assess both the fit and the kinematic profile of a particular permanent implant size. Upon deciding that a particular provisional implant component is too large for a given knee prosthesis, a surgeon can prepare the distal femur for the next smallest size using the cut slots provided in the already-mounted femoral provisional implant component. Advantageously, the femoral component in a knee prosthesis may be downsized quickly and with a minimum of additional bone resection using provisional orthopaedic implant components made in accordance with the present disclosure. Also advantageously, next-smaller sizes may be provided with only particular component portions downsized, such as the posterior condyles. Thus, a particular flexion/extension balance can be achieved in the knee prosthesis for a particular range of flexion while leaving other ranges of flexion unaffected.

In one form thereof, the present invention provides a knee prosthesis system comprising: a first provisional component having a first articular surface and a first bone contacting surface disposed opposite the first articular surface, the first bone contacting surface comprising: a first anterior surface defining a first, generally coronal anterior plane; a first distal surface defining a first, generally transverse plane; and a first posterior surface defining a first, generally coronal posterior plane, a first distance extending anteroposteriorly from the first posterior plane to the first anterior plane, the first provisional component further comprising a posterior cut slot defining a posterior cut width and adapted to receive a cutting instrument; a second component having a second articular surface defining a second articular surface geometry and a second bone contacting surface disposed opposite the second articular surface, the second bone contacting surface comprising: a second anterior surface defining a second, generally coronal anterior plane; a second distal surface defining a second, generally transverse plane; and a second posterior surface in a second, generally coronal posterior plane, a second distance extending anteroposteriorly from the second posterior plane to the second anterior plane; and the second distance less than the first distance by an amount equal to the posterior cut width.

In another form thereof, the present invention provides a method of implanting a knee prosthesis, the method comprising: selecting a larger provisional component from a kit of components; resecting a femur to receive the larger provisional component; implanting the larger provisional component onto the femur; articulating the femur to assess at least one kinematic characteristic of the knee prosthesis with the larger provisional component; determining that the larger provisional component is too large; selecting a smaller component from the kit of components; without removing the larger provisional component, at least partially further resecting the femur to fit the smaller component; and replacing the larger provisional component with the smaller component.

In yet another form thereof, the present invention provides a method of implanting a knee prosthesis, the method comprising: providing a first provisional component having a first articular surface and a first bone contacting surface disposed opposite the first articular surface, the first bone contacting surface having a first geometry comprising: a first anterior surface defining a first anterior coronal plane; a first distal surface defining a transverse plane and defining a first anteroposterior distal surface extent; a first posterior surface defining a first posterior coronal plane, a first anteroposterior distance extending from the first posterior coronal plane to the first anterior coronal plane; a first anterior chamfer surface extending between the first anterior surface and the first distal surface; a first posterior chamfer surface extending between the first posterior surface and the first distal surface; a posterior cut slot defining a posterior cut width; and a posterior chamfer cut slot defining a posterior chamfer cut width; resecting a femur so that the femur has a resected geometry corresponding to the first geometry, the step of resecting comprising: making a distal cut; making an anterior cut; making a posterior cut; making an anterior chamfer cut extending between the anterior cut and the distal cut; and making a posterior chamfer cut extending between the posterior cut and the distal cut; removably mounting the first provisional component to the resected femur; assessing a quality of fit between the first provisional component and the knee prosthesis; further resecting the posterior cut of the femur through the posterior cut slot, such that a second anteroposterior distance is defined between the anterior cut and the further resected posterior cut, the second anteroposterior distance less than the first anteroposterior distance; further resecting the posterior chamfer cut of the femur through the posterior chamfer cut slot; removing the first provisional component; providing a second prosthetic component having a second articular surface and a second bone contacting surface disposed opposite the second articular surface, the second bone contacting surface having a second geometry different than the first geometry, the second bone contacting surface comprising: a second anterior surface defining a second anterior coronal plane; a second distal surface defining a transverse plane and defining a second anteroposterior distal surface extent; a second posterior surface defining a second posterior coronal plane, the second anteroposterior distance defined between the second posterior coronal plane and the second anterior coronal plane; and after the steps of further resecting the posterior cut and further resecting the posterior chamfer cut, implanting the second component to the further resected femur.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

The present disclosure provides a set of provisional orthopaedic implant components with integral cutting guides, where the cutting guides are sized and oriented to correspond to a resected bone profile appropriate for the next smallest size of a provisional or permanent orthopaedic implant component. In one exemplary embodiment, only posterior cuts are needed to downsize from a relatively larger component to a relatively smaller component, with the smaller component adapted to alter or "fine-tune" a particular parameter of flexion/extension balance in a knee prosthesis.

In the following discussion, "proximal" refers to a direction toward the torso of a patient, while "distal" refers to the opposite direction of proximal, i.e., away from the torso of the patient. "Anterior" refers to a direction toward the front of a patient, while "posterior" refers to the opposite direction of anterior, i.e., toward the back of the patient.

While the embodiments detailed herein are shown and described with regard to a right knee, it will be appreciated that the present disclosure is equally applicable to a left knee configuration. Moreover, it will be appreciated that the principles of the present disclosure are also applicable to other mammalian joints, such as the human hip, shoulder, elbow, ankle, or the like.

Figure 1A:
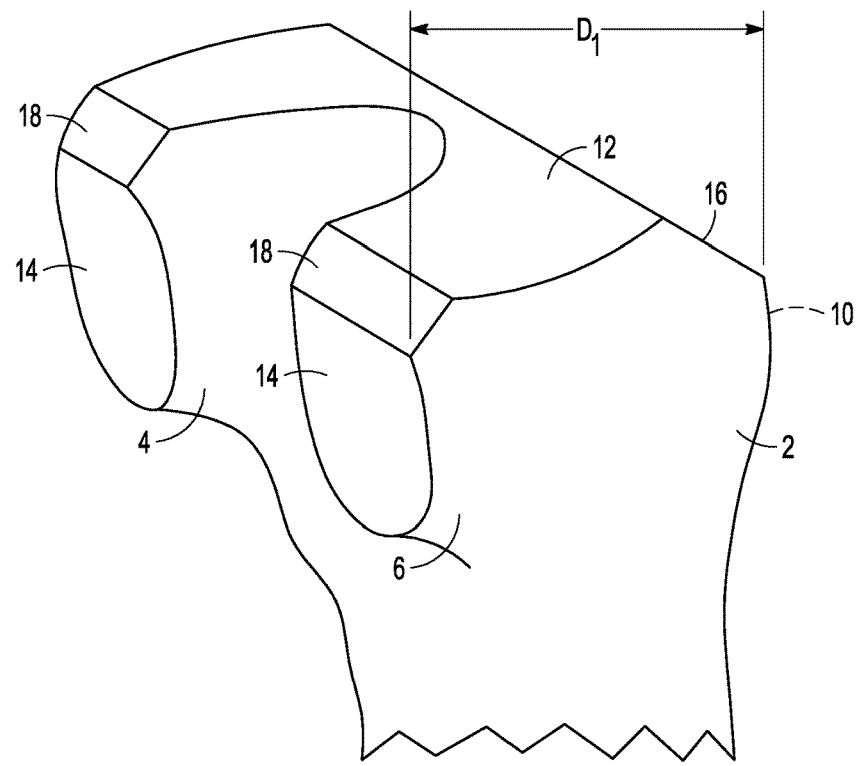
FIG. 1A is a perspective view of a distal femur after an initial resection.

Referring now to FIG. 1A, femur 2 includes lateral condylar portion 4 and medial condylar portion 6, each of which has been subject to initial resections to accommodate a first femoral orthopaedic implant component as described below. The initial resections of femur 2 are performed by any suitable methods and/or apparatuses. One such suitable method and apparatus is described in U.S. Pat. No. 5,743,915 filed Mar. 25, 1997 and entitled FEMORAL MILLING INSTRUMENTATION FOR USE IN TOTAL KNEE ARTHROPLASTY WITH OPTIONAL CUTTING GUIDE ATTACHMENT, which is commonly assigned with the present application, the entire disclosure of which is hereby expressly incorporated herein by reference.

An exemplary method and apparatus is the described in 4-in-1 Femoral A/P Sizing and Rotation Guide, available from Zimmer located at P.O. Box 708, 1800 West Center Street, Warsaw, Ind. 46581-0708. The 4-in-1 Femoral A/P Sizing and Rotation Guide and its method of use is described in the Surgical Technique entitled "Zimmer MIS Multi-Reference 4-in-1 Femoral Instrumentation," a copy of which is submitted on even date herewith, the entire disclosure of which is hereby expressly incorporated by reference herein. As described in the Surgical Technique, the processing of making initial bone resections includes: making an incision exposing the distal condyles; drilling a hole in the center of the patellar sulcus to establish alignment with the intramedullary canal of the femur; placing an intramedullary rod into the drilled hole; using an initial cut guide to make the first, distal cut (such as distal cut 12 shown in FIGS. 1A and 1B, which may be normal to the longitudinal axis of the intramedullary rod); measuring the femur size and placing an appropriately sized 4-in-1 cut guide on the distal cut surface; and making the remaining anterior, posterior and chamfer cuts (such as cuts 12, 14, 16, 18 shown in FIGS. 1A and 1B) by guiding a cutting instrument with the cut slots in the cut guide.

Figure 1B:
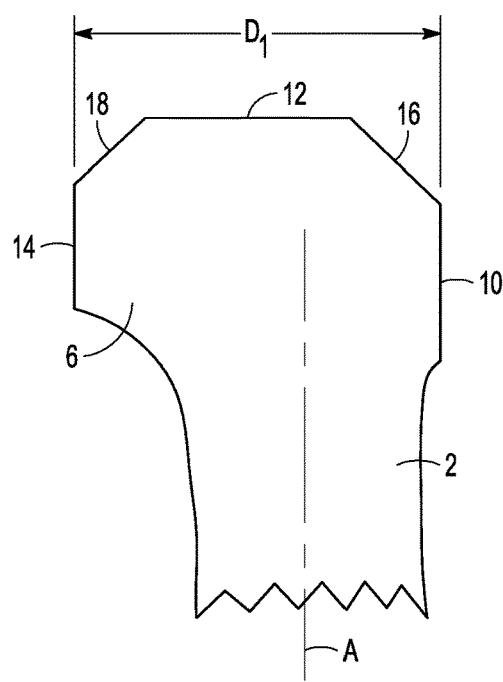
FIG. 1B is a side elevation view of the resected femur of FIG. 1A, viewed in a sagittal plane.

In the illustrative embodiment of FIGS. 1A and 1B, femur 2 includes five initial cuts which prepare femur 2 for receipt of a first, larger femoral prosthesis 20 (FIGS. 2A-4). Anterior cut 10 forms a coronal planar surface, i.e., a planar surface extending in generally proximal/distal and medial/lateral directions, and generally parallel to femoral axis A (FIG. 1B). Distal cut 12 forms a transverse planar surface, i.e., a planar surface that is substantially normal to femoral axis A and extends in generally medial/lateral, and anterior/posterior directions. In the illustrated embodiment, planes 10, 12 form a slightly oblique angle, i.e., slightly more than 90 degrees, though it is contemplated that planes 10, 12 may be perpendicular or may form an acute angle as required or desired for a particular application.

Posterior cut 14 extends along a generally coronal plane, similar to anterior cut 10. As shown in FIG. 1A, posterior cut 14 spans lateral and medial condylar portions 4, 6 to form a common but disjointed plane therebetween. In the illustrated embodiment, an angle between posterior cut 14 and distal cut 12 is between about 91 degrees and 93 degrees, though larger angles are contemplated. Posterior cut 14 also forms a highly acute angle with anterior cut 10, i.e., slightly more than zero degrees, so that a plane defined by anterior cut 10 diverges with a plane defined by posterior cut 14 as the planes extend proximally. This divergence facilitates a mediolateral or distal-to-proximal installation of a femoral prosthetic component. However, it is contemplated that other angular arrangements may be used, such as parallel or proximally converging anterior and posterior cuts 10, 14, as required or desired for a particular application.

As used herein, "coronal plane," "transverse plane," and "sagittal plane" (described below) are generally perpendicular to one another, but may vary in any direction by a small amount, such as by up to about five degrees. For example, although anterior cuts 10, 14 are not parallel as described above, cuts 10, 14 both may be said to lie in a generally coronal plane.

Anterior chamfer 16 extends between anterior cut 10 and distal cut 12. Posterior chamfer 18 extends between posterior cut 14 and distal cut 12. Anterior and posterior chamfers 16, 18 may be sized and angularly oriented in any suitable manner. In an exemplary embodiment, anterior chamfer 16 remains substantially constant for a wide variety of femoral component sizes so that no recutting of anterior chamfer 16 is necessary to fit a smaller femoral component. On the other hand, posterior chamfer 18 may change from size to size to accommodate changes in the geometry of different femoral components (as described in detail below).

1. Provisional Implants for Posterior Recutting—Construction

Figure 6A:
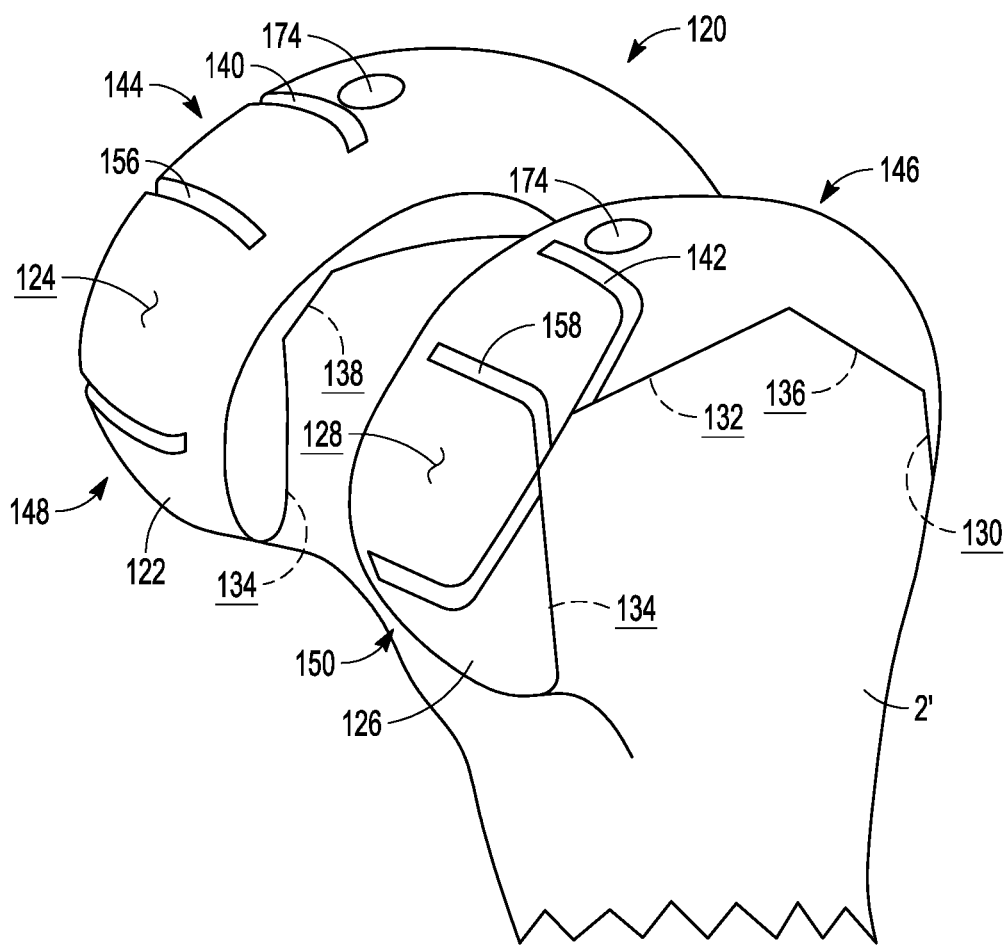
FIG. 6A is a perspective view of the distal femur after completion of the resection of FIG. 5, with a provisional component of the next-smallest size mounted to the distal femur.
Figure 6B:
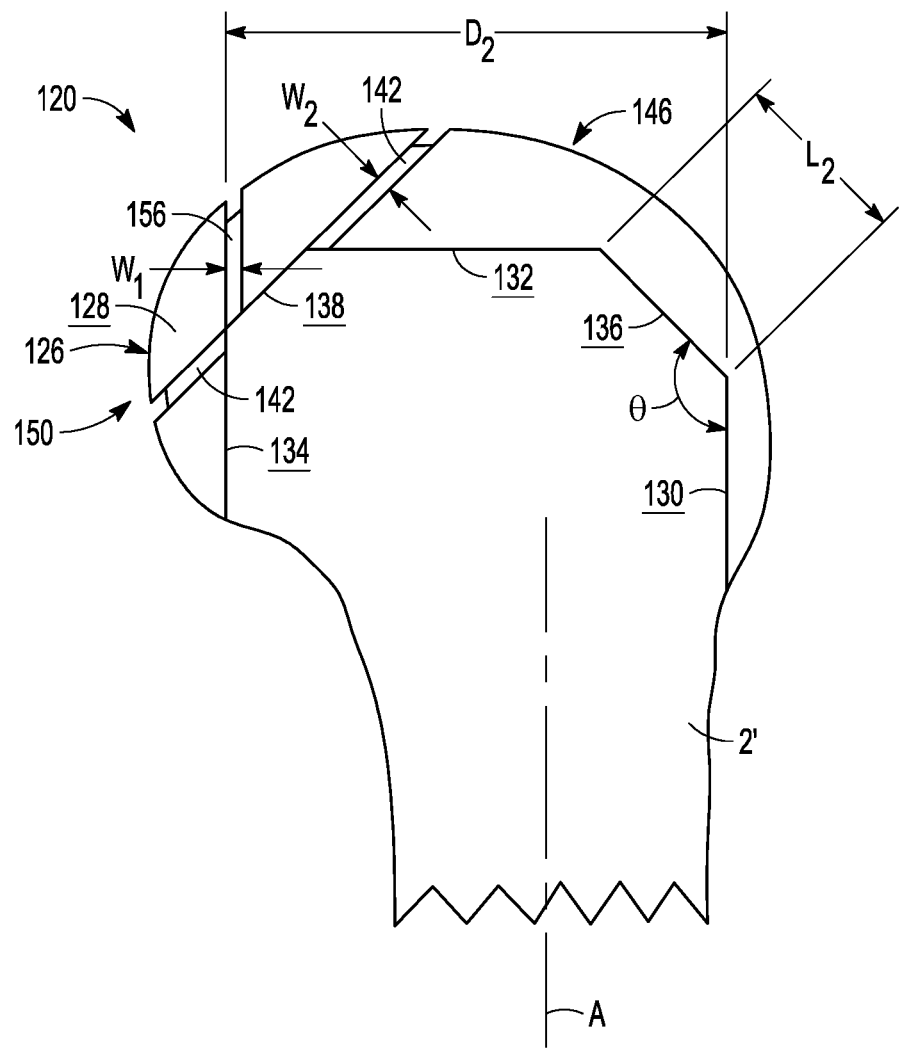
FIG. 6B is an elevation view of the distal femur and permanent femoral component shown in FIG. 6A, taken from a sagittal plane.

After the initial resection of femur 2 as described above, femur 2 defines anteroposterior extent $D_1$ which is the distance between posterior cut 14 and the distal-most portion of anterior cut 10 (i.e., the junction between anterior cut 10 and anterior chamfer 16). As shown in FIG. 2B, anteroposterior extent $D_1$ accommodates a first, relatively larger provisional femoral component 20. Larger provisional component 20 is part of a set or kit of provisional components having varying sizes, and is larger than smaller provisional component 120, which is the next-smallest size in the component set (as shown in FIGS. 6A and 6B, as described in detail below).

Larger provisional component 20 includes lateral condyle 22 having lateral articular surface 24, and medial condyle 26 having medial condyle articular surface 28. Disposed opposite articular surfaces 26, 28, provisional component 20 further defines bone contacting surfaces including anterior bone contacting surface 30, distal bone contacting surface 32, posterior bone contacting surface 34, anterior bone contacting chamfer 36, and posterior bone contacting chamfer 38. Bone contacting surfaces 30, 32, 34, 36, 38 are sized and oriented to correspond with anterior cut 10, distal cut 12, posterior cut 14, anterior chamfer 16 and posterior chamfer 18 of femur F, respectively (FIG. 1B), so that larger provisional component 20 forms a snug fit with resected femur 2 and covers a large proportion of the bone surfaces exposed by cuts 10, 12, 14, 16, 18.

To ensure this snug femur/component fit, provisional component 20 is designed to create a small gap between anterior and posterior chamfers 16, 18 and anterior and posterior chamfer surfaces 36, 38, respectively. These gaps ensure that contact between chamfers 16, 18 and chamfer surfaces 36, 38 cannot interfere with fully seated contact between anterior, distal and posterior cuts 10, 12, 14 and anterior, distal and posterior surfaces 30, 32, 34 respectively, even if there are variations in cut tolerances. Similarly to posterior cut 14 and posterior chamfer 18, posterior surface 34 and posterior chamfer surface 38 of larger provisional component 20 extend across both lateral condyle 22 and medial condyle 26, so that each of surfaces 34, 38 lie in a single plane but form two discontinuous or disjointed surfaces.

Larger provisional component 20 is paired with permanent component 70 (FIG. 7A), in that provisional component 20 is sized and shaped to have substantially identical bone-contacting and articular surfaces as permanent component 70. For example, angle $\Theta$ is defined between anterior surfaces 30 and anterior chamfer surfaces 36 of both provisional component 20 and permanent component 70. Thus, when a surgeon implants larger provisional component 20 onto resected femur 2, the interaction of bone contacting surfaces 30, 32, 34, 36, 38 with respective cuts 10, 12, 14, 16, 18 can be expected to mimic the corresponding contact interaction between permanent component 70 and femur 2. Similarly, the articulation characteristics (i.e., "kinematic profile") of lateral and medial condyle articular surfaces 24, 28 when articulating with adjacent articular surfaces (such as a tibial bearing component) can be expected to mimic the corresponding articular interaction of permanent femoral component 70 with those same articular surfaces. As will be described in more detail below, this mimicry allows larger provisional component 20 to be used as a proxy for permanent component 70. Thus, a surgeon can intraoperatively evaluate component sizing and configuration, while retaining the ability to use provisional component 20 as a cut guide to for downsizing to a smaller provisional component (as appropriate).

Figure 2A:
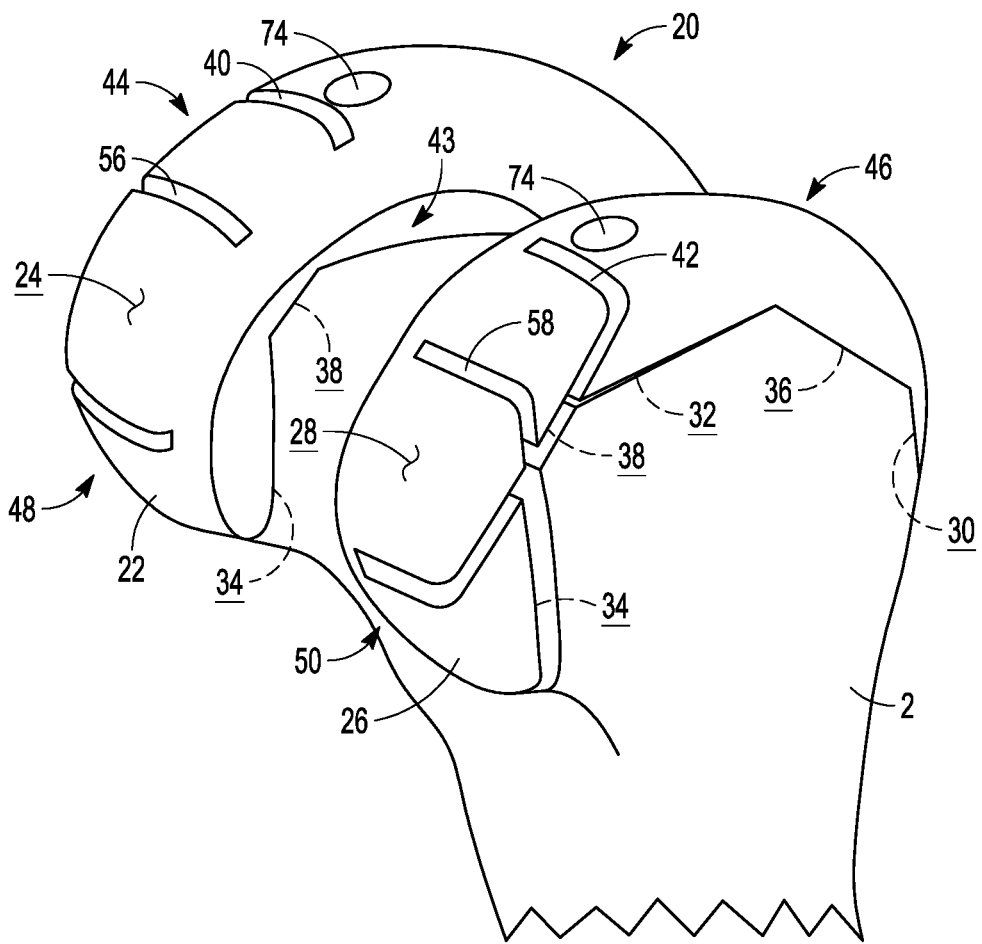
FIG. 2A is a perspective view of the distal femur shown in FIG. 1A, shown with an initial larger provisional orthopaedic implant with integral cutting guide adapted for posterior and posterior chamfer recuts in accordance with the present disclosure.
Figure 2B:
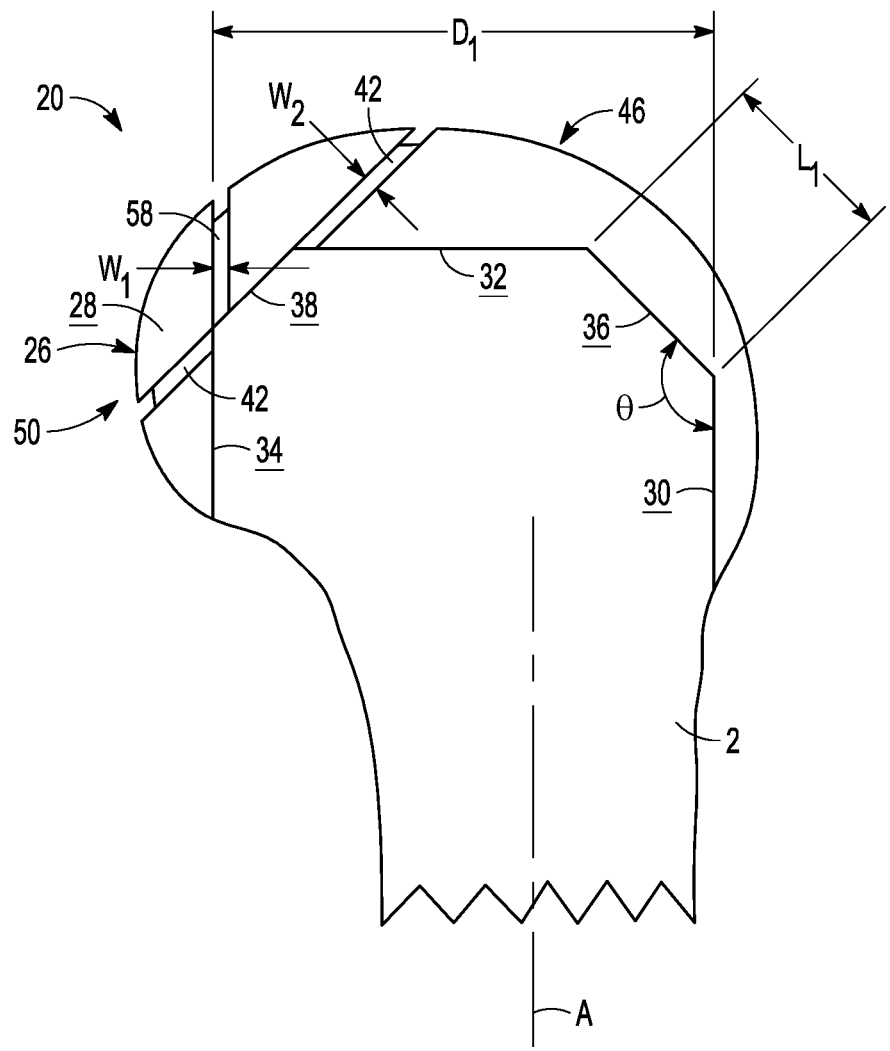
FIG. 2B is a side elevation view of the distal femur and provisional orthopaedic implant shown in FIG. 2A, taken from a sagittal plane.

Referring still to FIGS. 2A and 2B, larger provisional component 20 includes lateral and medial posterior chamfer cut slots 40, 42 extending from distal portions 44, 46 of lateral and medial condyles 22, 26 to posterior portions 48, 50 thereof. In the illustrated embodiment, lateral and medial posterior chamfer cut slots 40, 42 are substantially identical, and are mirror images of one another about a sagittal plane. Lateral posterior chamfer cut slot 40 extends into condyle 22 from lateral to medial without extending entirely through lateral condyle 22. Similarly, medial posterior chamfer cut slot 42 extends from medial to lateral into medial condyle 26 without passing entirely through medial condyle 26. Conversely, it is contemplated that lateral cut slot 40 could extend from intercondylar fossa 43 (formed between condyles 22, 26 as shown in FIG. 2A) in a lateral direction, and that medial cut slot 42 could extend from intercondylar fossa 43 in a medial direction.

As best seen in FIG. 2B, posterior chamfer cut slots 40, 42 define slot width $W_2$, which remains constant across substantially the entire longitudinal extent of cut slots 40, 42. Posterior chamfer cut slots 40, 42 are substantially linear, such that the bounds of width $W_2$ define planar surfaces extending mediolaterally into cut slots 40, 42. As will be described in more detail below, posterior chamfer cut slots 40, 42 are sized and oriented to facilitate the resection of posterior chamfer 18 to prepare femur 2 to accept smaller provisional component 120 (FIG. 6B).

Figure 3:
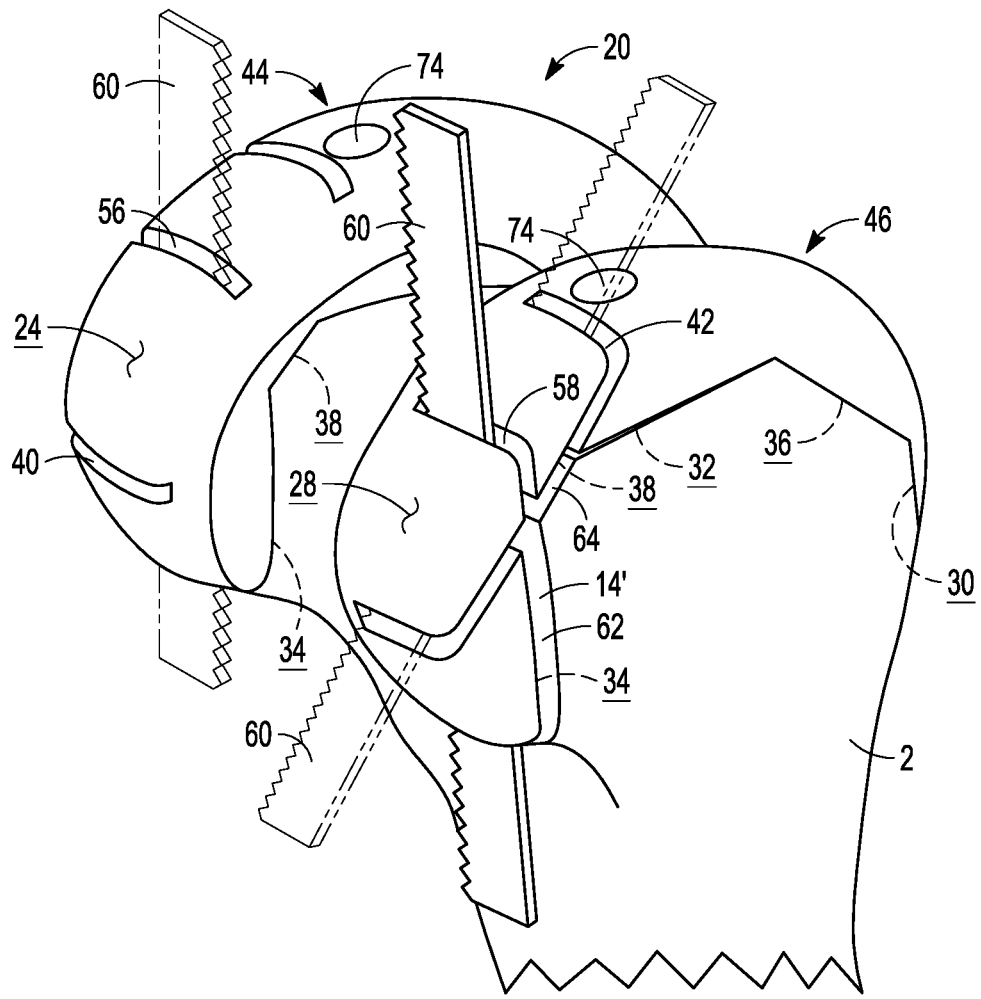
FIG. 3 is a perspective view of the distal femur and provisional orthopaedic implant shown in FIG. 2A, illustrating cutting instruments disposed in cut slots of the provisional orthopaedic implant.

Larger provisional component 20 further includes lateral posterior cut slot 56 and medial posterior cut slot 58 (FIG. 2A). Posterior cut slots 56, 58 are similar to posterior chamfer cut slots 40, 42, except that posterior cut slots 56, 58 are positioned and oriented to correspond with posterior surface 34 of larger provisional component 20 (and, concomitantly, with posterior cut 14). Lateral and medial posterior cut slots 56, 58 each extend substantially linearly along a coronal plane, and define slot width $W_1$. In the illustrated embodiment, width $W_2$ of cut slots 40, 42 is larger than width $W_1$ of cut slots 56, 58 to accommodate the particular changes in geometry between larger provisional component 20 (FIG. 2B) and smaller provisional component 120 (FIG. 6B). However, it is contemplated that width $W_1$ may be equal to width $W_2$ as required or desired for a particular application. In an exemplary embodiment, $W_1$ and $W_2$ are about 1 mm, which is large enough to accommodate a thickness of saw blade 60 (FIG. 3). It is contemplated that the total width of resected bone may be larger than widths of cut slots $W_1$ and $W_2$, as described below.

Similar to cut slots 40, 42, cut slots 56, 58, do not extend entirely through lateral and medial condyles 22, 26, respectively. As described in detail below, posterior cut slots 56, 58 are sized and positioned to facilitate the further resection of posterior cut 14 to prepare femur 2 to accept smaller provisional component 120 (FIG. 6B). However, it is contemplated that cut slots 40, 42, 56, 58 can extend across the entirety of bone surfaces 14, 18, as discussed below.

2. Provisional Implant Recutting System—Use

In use, a surgeon first identifies a range of prosthetic femoral implant component sizes appropriate for a particular patient. Such identification can be accomplished in any suitable manner, such as through preoperative imaging including radiography, magnetic resonance imaging (MRI) or computer tomography scanning (CT scanning), for example. Alternatively, a range of prosthetic component sizes can be identified intraoperatively.

The surgeon initiates the knee arthroplasty procedure, including performing cuts 10, 12, 14, 16, 18 based on the largest of the range of femoral implant sizes previously identified (as described above). The largest size of the identified range of sizes is initially provided by the surgeon because this approach conserves as much natural bone as practical. Specifically, if a larger initial component is not a proper fit, a next component choice will be the next-smaller component. Normally only a single recutting procedure is necessary, but additional smaller components may be employed if a single recutting procedure proves insufficient. As a result of this "downsizing" approach, the surgeon resects only as much bone as necessary.

As used herein, "providing" prosthetic components such as provisional component 20 refers to procurement thereof, such as from a kit or operating-room container or storage receptacle. Prior to the step of providing component 20, the surgeon may or may not be involved with acquisition from the manufacturer, receipt of shipments, inventorying, or other procurement activities occurring outside the operating room environment.

In the illustrated embodiment, the initially-chosen, relatively larger component corresponds to larger provisional component 20. Thus, provisional component is the first provisional component mounted to femur 2 after the initial resection is complete. Once larger provisional component 20 is securely mounted to femur 2 (as shown in FIGS. 2A and 2B), such as with pins, press fit, temporary adhesive, bone screws or the like, the surgeon assesses the quality of fit between larger provisional component 20 and the rest of the structures in the knee and knee prosthesis.

If the surgeon is satisfied with the fit, the knee may then be articulated through a range of motion to assess interaction between lateral and medial condyle articular surfaces 24, 28 and corresponding articular surfaces of a tibial bearing component or natural tibial surface (not shown). Patellofemoral articulation of a natural or prosthetic patella (not shown) with the anterior portion of provisional component 20 may also be assessed at this time. Tension on natural or prosthetic knee soft tissue, such as the medial and lateral collateral ligaments and anterior and posterior cruciate ligaments, may also be evaluated when the knee is stationary and/or during knee articulation. For surgical procedures in which one or more ligaments are resected, such as the anterior and/or posterior cruciate ligaments, only those ligaments remaining after the resection are evaluated for proper tension.

If ligament tension, kinematic profile, soft tissue balancing, and other considerations are satisfactory to the surgeon, peg hole drill guides 74 formed in larger provisional component 20 (FIG. 2A) may be used to drill peg holes in femur 2, larger provisional component 20 is removed from femur 2, and the substantially identically sized permanent femoral component 70 (FIG. 7A) is attached to femur 2 in the same location and orientation. Larger permanent component 70 may include at least one peg 72 (FIG. 7A) which is received in the previously drilled peg holes to aid in fixation of component 70 to femur 2. However, in some embodiments (such as in relatively smaller-sized prostheses), no pegs are provided in the permanent femoral component, such that no peg hole drill guides need to be provided on the corresponding provisional femoral component.

In some instances, however, the surgeon may not be satisfied with the fit and/or kinematics of larger femoral component 20. Moreover, given that larger provisional component 20 is the largest in a range of component sizes previously identified by the surgeon as being potentially appropriate for femur 2 (as described above), larger provisional component 20 may sometimes prove to be too large. For example, an implant may be considered too large if one or more ligaments in the operative knee have higher-than-optimal tension, if the knee prosthesis has an undesirable kinematic profile, if the knee prosthesis exhibits poor soft tissue balance within the knee, or if the implant laterally or medially overhangs any of the respective cuts 10, 12, 14, 16, 18 made in femur F.

In other instances, larger provisional component 20 may be found to be of proper overall size, and may have optimal soft-tissue balance in extension, but is subsequently found to exhibit a higher-than-optimal tension when the knee is articulated to a flexion orientation. In this case, larger provisional component 20 can be used to prepare femur 2 to accept a next-smallest component in the range of component sizes which maintains certain geometries of larger provisional component 20, but features a smaller posterior compartment. This preserves the established proper extension tension while reducing the higher-than-optimal flexion tension as described in detail below.

Turning now to FIG. 3, posterior chamfer cut slots 40, 42 and posterior cut slots 56, 68 of larger provisional component 20 may be used in a "recutting" procedure to prepare femur 2 to receive smaller provisional component 120 (FIGS. 6A and 6B, described in detail below). A cutting instrument, such as saw blade 60 shown in FIG. 3, is passed into each of cut slots 40, 42, 56, 58, so that blade 60 contacts and resects bone from femur 2 proximate posterior cut 14 and posterior chamfer 18, respectively. Blade 60 is passed through the entirety of cut slots 40, 42, 56, 58, such that the additional bone stock resected from femur 2 during the recutting procedure is equal to widths $W_1$ and $W_2$ of cut slots 56, 58 and 40, 42 respectively. That is to say, blade 60 is brought into contact with each of the faces of cut slots 56, 58 and 40, 42 defining widths $W_1$ and $W_2$, thereby ensuring that blade 60 reaches all of the outer extents of cut slots 40, 42 and 56, 58.

Figure 4:
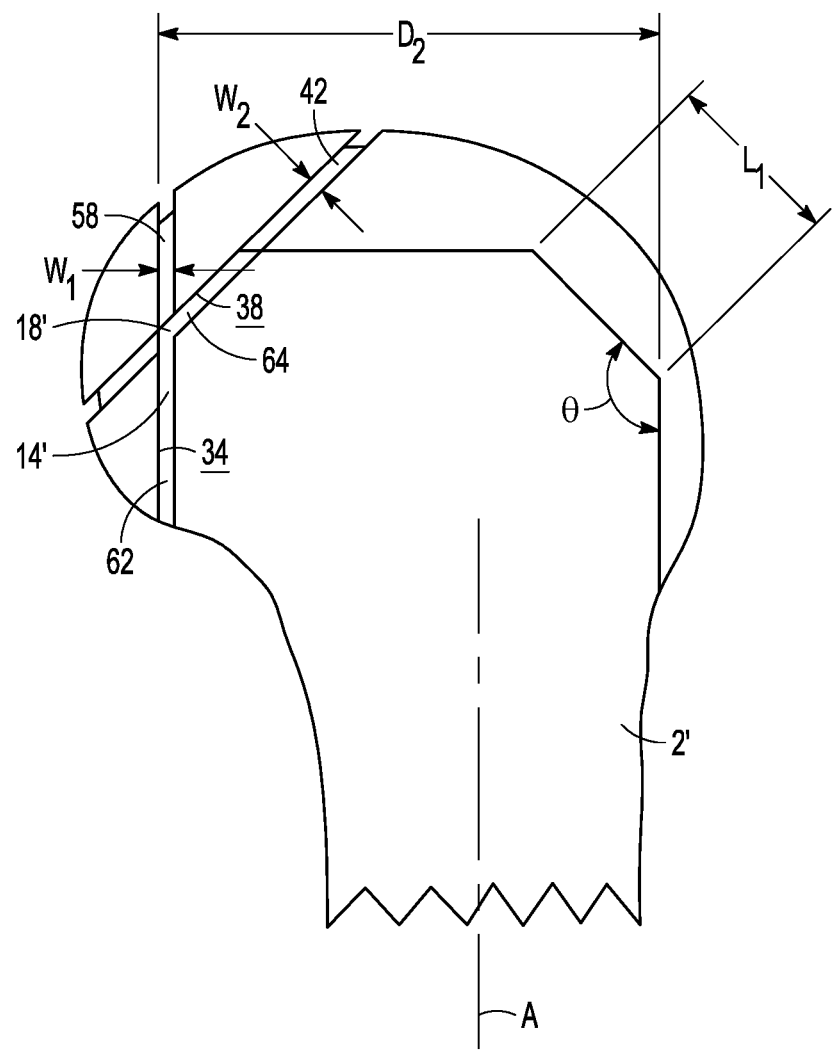
FIG. 4 is a side elevation view of the distal femur and provisional orthopaedic implant shown in FIG. 3, taken from a sagittal plane, after the cutting instruments have been engaged with the cut slots.

Referring now to FIG. 4, femur 2' is shown after the recutting procedure is complete. Femur 2' has posterior gap 62 between the surface of posterior cut 14' and posterior surface 34 of larger provisional component 20. Similarly, posterior chamfer gap 64 is defined between the surface of posterior chamfer 18 and posterior chamfer surface 38 of larger provisional component 20. Because gaps 62, 64 are created by blade 60 passing through the entireties of cut slots 40, 42, 56, 58 as described above, gaps 62, 64 define widths $W_1$ and $W_2$, respectively. In one embodiment, width $W_1$ is equal to the reduction in size of smaller provisional component 120 as compared to larger provisional component 20 at posterior surfaces 34, 134, while width $W_2$ is equal to the reduction in size of smaller provisional component 120 as compared to larger provisional component 20 at posterior chamfers 38, 138. Thus, after blade 60 has been passed through cut slots 40, 42, 56, 58, femur 2' is prepared to receive smaller component 120. Thus, cut slots 40, 42, 56, 58 define widths $W_2$, $W_1$, which in turn define the cut widths, i.e., the total amount of additional resection at posterior cut 14' and posterior chamfer 18' as compared to posterior cut 14 and posterior chamfer 18.

In an exemplary embodiment, it is contemplated that cut slots 40, 42, 56, 58 may be inwardly spaced on provisional component 20 to define cut widths that are greater than widths $W_2$, $W_1$. When so spaced, blade 60 may cut an entirely new slot in femur 2, rather than expanding an existing cut (such as cuts 14, 18). When this entirely new slot is cut, bone remains on either side of the new cut. Thus, the total amount of bone resection is not be equal to widths $W_2$, $W_1$ of cut slots 40, 42, 56, 58, but rather would be equal to widths $W_2$, $W_1$ plus the inward spacing from the cut slot to the bone contacting surface. Moreover, cut slots 40, 42, 56, 58 may placed at any location on provisional component 20, and this placement may cooperate with widths $W_2$, $W_1$ to define the total additional resection of femur 2. For example, provisional component 20 having cut slots widths $W_2$, $W_1$ of about 1 mm (as described above) may be positioned to define an overall cut width of between 1 mm and 4 mm or more. In yet another alternative, cut slots 40, 42, 56, 58 may be outwardly spaced on provisional component 20 so that the total overall cut widths are less than widths $W_2$, $W_1$.

Figure 5:
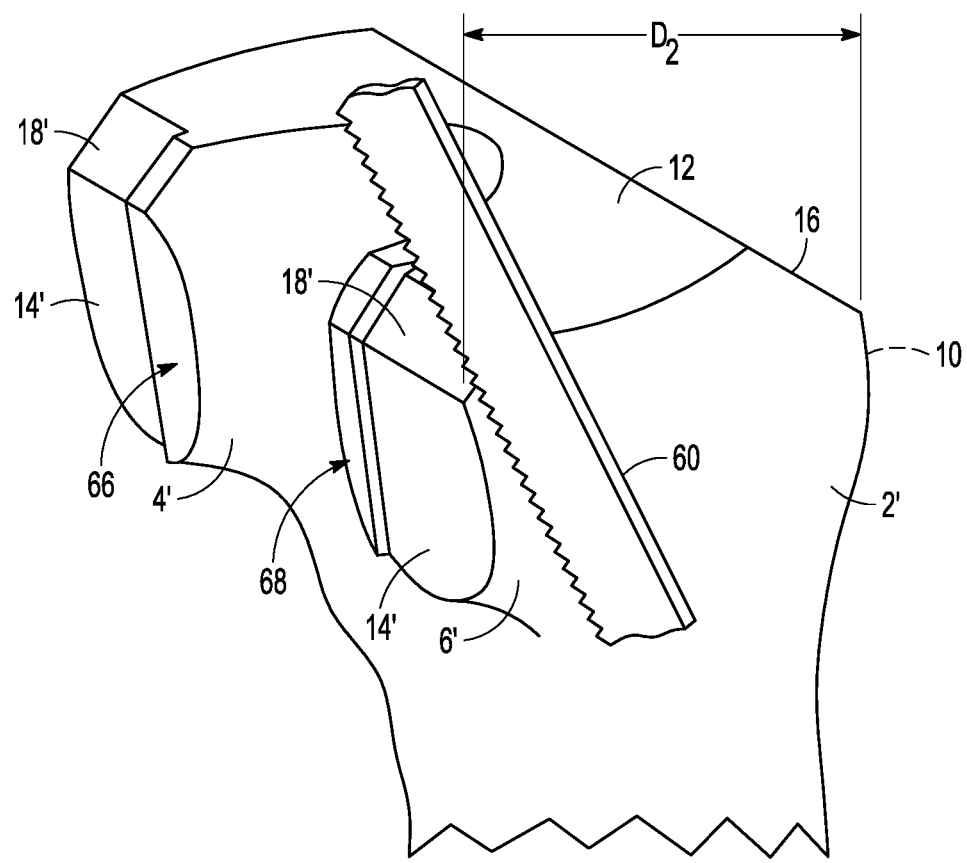
FIG. 5 is a perspective view of the distal femur shown in FIG. 4, illustrating a cutting instrument completing the resection begun by engaging the cutting instrument with the cut slots of the provisional orthopaedic implant as shown in FIG. 3.

Once the femoral recutting process is complete, i.e., after blade 60 has been passed through cut slots 40, 42, 56, 58 (FIG. 3), larger provisional component 20 is removed from newly resected femur 2' to expose lateral and medial bone shoulders 66, 68, as shown in FIG. 5. Shoulders 66, 68 are left behind, resulting from cut slots 40, 42, 56, 58 not passing entirely through lateral and medial condyles 22, 26 as described above. As illustrated in FIG. 5, bone shoulders 66, 68 are removed using blade 60 after larger provisional component 20 is detached from femur 2'. Removal of shoulders 66, 68 can be effected using posterior cut 14' and posterior chamfer 18' as guide surfaces, thereby rendering posterior cut 14 and anterior chamfer 18 substantially planar and continuous across lateral and medial condylar portions 4' and 6' after shoulders 66, 68 are completely removed. Newly resected femur 2' defines an overall anteroposterior resection distance $D_2$ that is less than anteroposterior resection distance $D_1$ by an amount equal to width $W_1$, while posterior chamfer 18' is inset toward femoral axis A by a distance equal to width $W_2$.

It is contemplated that cut slots 40, 42, 56, 58 may be adapted to allow blade 60 to pass across the entirety of surfaces 14, 18 respectively, such as by forming condyles 22, 26 with an oversized mediolateral profile to allow cut slots 40, 42, 56, 58 to be made longer. In this case, no shoulders would remain after removal of larger provisional component 20 and posterior cut 14' and posterior chamfer 18' would be completely planar.

Turning now to FIGS. 6A and 6B, anteroposterior resection distance $D_2$ is the proper distance for securely mounting smaller provisional component 120 to femur 2' with a snug fit. Smaller provisional component 120 is similar to larger provisional component 20, except that smaller provisional component 120 has a smaller interior geometry adapted to fit femur 2' after recutting (as described in detail below).

Smaller provisional component 120 includes lateral condyle 122 having lateral condyle articular surface 124, and medial condyle 126 having medial condyle articular surface 128. Articular surfaces 124, 128 are smaller than articular surfaces 24, 28 of larger femoral component 20, consistent with the smaller size of smaller provisional component 120 (see FIG. 7A). Smaller provisional component 120 defines bone contacting surfaces disposed opposite articular surfaces 124, 128, including anterior bone contacting surface 130, distal bone contacting surface 132, and posterior bone contacting surface 134. Anterior chamfer bone contacting surface 136 extends between anterior surface 130 and distal surface 132, and posterior chamfer bone contacting surface 138 extends between posterior surface 134 and distal surface 132.

As shown in FIG. 6B, anteroposterior extent $D_2$ extends between posterior surface 134 and the distal-most point of anterior surface 130. The angular arrangements of the various respective surfaces are similar to larger provisional component 20, and are not repeated here. Turning to FIG. 6A, smaller provisional component 120 includes lateral posterior chamfer cut slot 140 and medial posterior chamfer cut slot 142, each extending between the distal portions 144, 146 of lateral and medial condyles 122, 126 and posterior portions 148, 150 of lateral and medial condyles 122, 126, respectively. Lateral and medial posterior cut slots 156, 158 extend partially through condyles 122, 126 in a coronal plane, similar to lateral and medial posterior cut slots 56, 58 described above.

Posterior cut slots 156, 158 define width $W_1$, which is identical to width $W_1$ of cut slots 56, 58. Similarly, cut slots 140, 142 define width $W_2$, which is identical to width $W_2$ of cut slots 40, 42. However, it is contemplated that cut slots 140, 142, 156, 158 of smaller femoral component 120 may have different widths from corresponding cut slots 40, 42, 56, 58 of smaller femoral component 120, as required or desired for a particular design or pair of sizes within a provisional component set.

With smaller provisional component 120 removably mounted to femur 2', the knee is again articulated through a range of motion to assess the quality of fit between smaller provisional component 120 and the knee and/or knee prosthesis. If the quality of fit is determined to be satisfactory, smaller provisional component 120 is removed and replaced with smaller permanent component 170 (FIG. 7A) after peg holes are drilled through peg hole drill guides 174 (FIG. 6A). Similar to larger permanent component 70, smaller provisional component 170 may include at least one peg 172. Peg 172 fits the peg hole drilled through peg hole drill guides 174. In the illustrated embodiment, peg hole drill guides 174 may have the same anteroposterior orientation as peg hole drill guides 74 of larger provisional component 20, so that drill guides 74, 174 are substantially coaxial when components 20, 120 are aligned in a sagittal plane, i.e., when anterior surfaces 30, 130 are aligned and distal surfaces 32, 132 are aligned. It is noted that alignment in a sagittal plane occurs when smaller provisional component 120 is mounted to femur 2' after larger provisional component 20 was mounted to femur 2, as described above. Thus, holes drilled through either of guides 74, 174 will advantageously fit either of pegs 72, 172 when one of components 20, 120 is snugly secured to femurs 2, 2' respectively.

If smaller provisional component 120 is still too large, cut slots 140, 142, 156, 158 may be employed in a similar manner to cut slots 40, 42, 56, 58 of larger provisional component 20 to further resect femur 2' at posterior cut 14' and posterior chamfer 18'. This further resection results in femur 2' being prepared to receive the next smaller implant size as compared to smaller provisional component 120. Moreover, further resection using cut guides formed in any mounted provisional implant component of the present disclosure will prepare the femur to fit the next smallest provisional component. Thus, this "downsizing" procedure may be performed as many times as necessary to achieve a desired kinematic profile, ligament tension, soft tissue balance, etc.

Permanent component 70 may be part of a set of components, with each component of the set adapted to fit the same resected femoral surface. Thus, a surgeon may have a range of components similar to larger permanent component 70 to choose from in seeking desired prosthesis characteristics. If the surgeon is dissatisfied with every component offered in the set including larger component 70, larger prosthetic component 20 may be used to create a new resected profile (i.e., the profile of femur 2' as described above). An entirely new set of components, including smaller permanent component 170 and other components adapted to fit the new resected profile, may then become available to the surgeon in his or her search for the desired prosthesis characteristics.

Figure 7A:
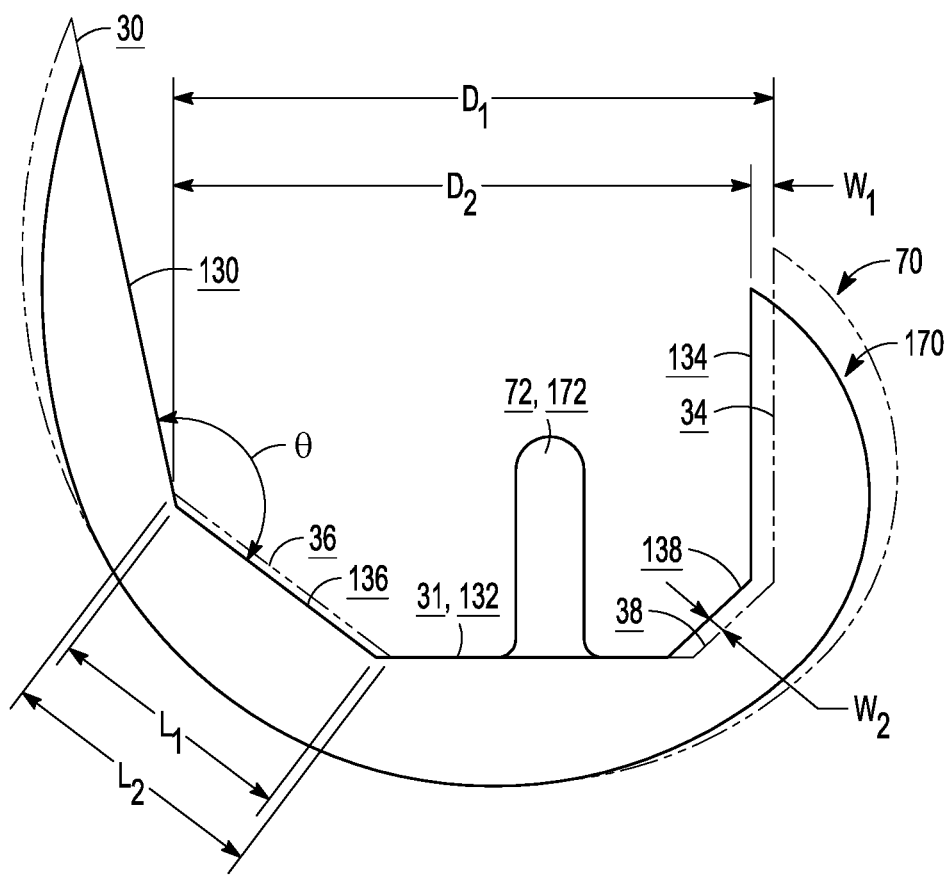
FIG. 7A is a side elevation view of a relatively smaller permanent femoral implant component, taken from a sagittal plane, with a relatively larger femoral component shown in dashed lines.

Advantageously, resecting femur 2 to accept a smaller implant only requires further resection at two of the five femoral cuts discussed above, namely, posterior cut 14 and posterior chamfer 18. As shown in FIG. 7A, anterior surfaces 30, 130 and distal surfaces 32, 132 of larger permanent implant 70 and smaller permanent implant 170, respectively, are substantially coincident with one another and therefore are adapted to cooperate with anterior cut 10 and distal cut 12 of femurs 2, 2' without any need for further resection. However, it is noted that distal cut 12 is made shorter along an anteroposterior direction by further resection of posterior chamfer 18.

In addition, anterior chamfer surfaces 36, 136 are nearly coincident, with surface 136 disposed only slightly anterior and distal of surface 36. Anterior chamfer surface 36 defines length $L_1$ in a sagittal plane (FIGS. 2B, 4 and 7A), while anterior chamfer surface 136 defines length $L_2$ in a sagittal plane (FIGS. 6B and 7A). $L_1$ is nearly the same as $L_2$, with $L_2$ slightly larger than $L_1$. In the illustrated embodiment, $L_2$ is larger than $L_1$ by between about 0.5 mm and about 1.1 mm. Thus, only a very small gap is created between anterior chamfer surface 136 of smaller provisional component 120 and anterior chamfer 16 of femur 2' when smaller provisional component 120 is mounted thereto. No further resection or other modification of anterior chamfer 16 is necessary when downsizing from larger provisional component 20 to smaller provisional component 120 intraoperatively. In certain embodiments, anterior chamfer surfaces 36, 136 may be completely coincident.

Moreover, anterior chamfer surfaces 36, 136 both define angle $\Theta$ with anterior surfaces 30, 130, respectively. Thus, larger components 20, 70 and smaller components 120, 170, which share a common angle $\Theta$ and have similar lengths $L_1$ and $L_2$ of anterior chamfer surfaces 36, 136 (as described above), have a similar overall anterior bone-contacting geometry, so that only the overall posterior bone-contacting geometry is altered to fit a smaller component size.

Thus, only posterior cuts 14, 14' and posterior chamfer cuts 18, 18' are further resected in order to accommodate the next-smaller sized provisional component. For example, as shown in FIG. 7A, larger permanent component 70 and smaller permanent component 170 have anteroposterior resection distances $D_1$, $D_2$, respectively corresponding to distances $D_1$, $D_2$ of femurs 2, 2'. In the illustrated embodiment, the difference between distance $D_1$ and $D_2$ is equal to $W_1$, so that an anterior shift of posterior surface 34 by a distance $W_1$ creates posterior surface 134. Similarly, the inward inset of posterior chamfer surfaces 38, 138 (toward axis A, along a line normal to surfaces 38, 138) is equal to width $W_2$ of lateral and medial posterior chamfer cut slots 40, 42, so that posterior chamfer surface 138 of smaller provisional component 120 fits femur 2' after using larger provisional component 20 to resect posterior chamfer 18 to create posterior chamfer 18'. In the context of components 20, 120, the inward inset of posterior chamfer surface 138 as compared to posterior chamfer surface 38 is measured when components 20, 120 are aligned, i.e., when anterior surfaces 30, 130 are coplanar and distal surfaces 32, 132 are coplanar.

Also advantageously, larger provisional component 20 may be used to assess the quality of fit between permanent component 70 and the surrounding structures of the knee and knee prosthesis, as described above, but may also be used to downsize larger provisional component 20 to smaller provisional component 120 without the use of any additional cut guides. Thus, the decision to downsize can be made intraoperatively and the ensuing recutting can begin immediately after the decision to downsize is made. No additional steps are necessary prior to beginning the additional needed resection.

Figure 7B:
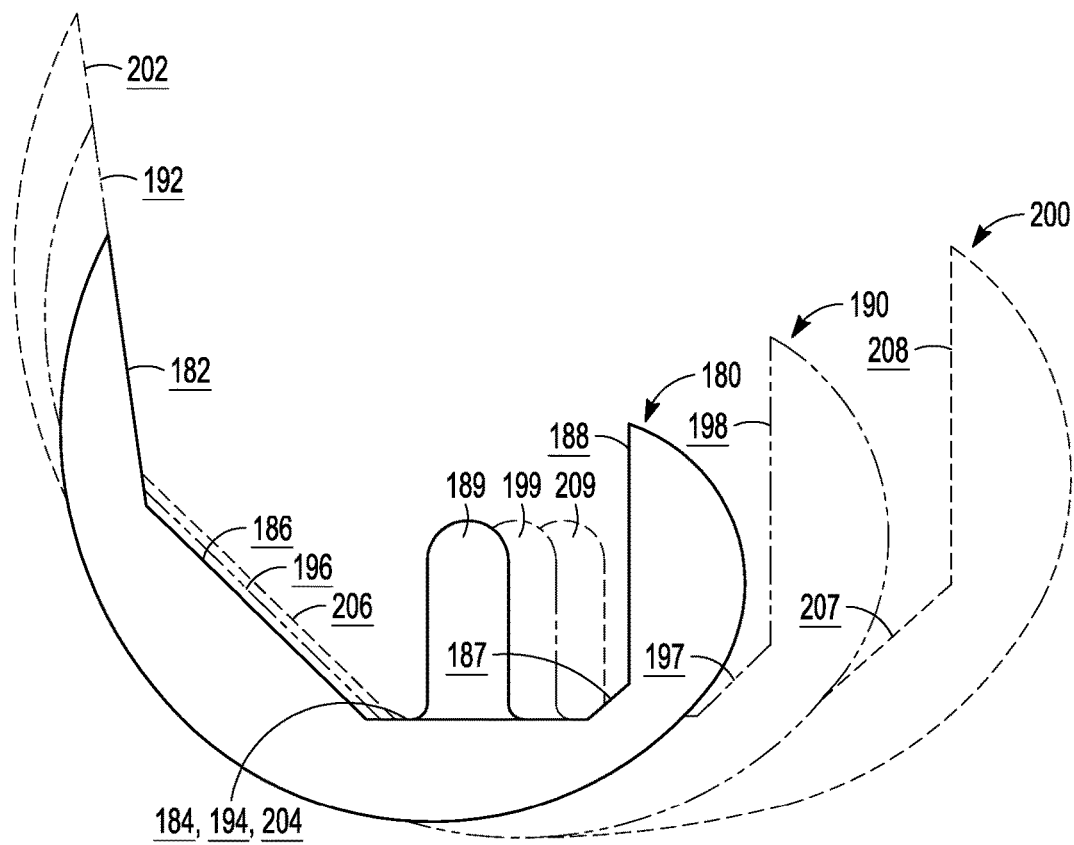
FIG. 7B is a side elevation view of a smallest permanent femoral implant component, taken from a sagittal plane, with largest and intermediate-sized femoral components shown in dashed lines.

Yet another advantage of the present disclosure is that a wide variety of implant sizes may be used while only altering posterior cut 14 and posterior chamfer 18 to switch between the range of sizes. As shown in FIG. 7B, smallest permanent implant 180 includes anterior chamfer surface 182 and distal surface 184. Anterior surface 182 is coplanar with anterior surfaces 192, 202 of intermediate component 190 and largest component 200, respectively, when the distal surfaces 184, 194, 204 are aligned in a sagittal profile. Similarly, distal surface 184 shares a common profile (i.e., planar extent and orientation) with anterior surfaces 194, 204, so that distal surfaces 184, 194, 204 are coincident when aligned in a sagittal profile. Moreover, all sizes in the range of sizes provided in a kit of permanent and provisional implants share these coplanar anterior surface and coincident distal surface arrangements.

In addition, anterior chamfers 186, 196, 206 of smallest, intermediate and largest components 180, 190, 200, respectively, are near enough to one another to allow a surgeon to downsize from largest component 200 to smallest component 180 without performing any additional anterior or distal resections or surgical steps. Instead, additional resections need only be made to posterior cut 14 and posterior chamfer 18 of femur 2 (FIGS. 1A and 1B) to accommodate posterior chamfer surfaces 187, 197, 207 and posterior surfaces 188, 198, 208 of smallest, intermediate size, and largest components 180, 190, 200, respectively.

Alternatively, only a posterior recut may be necessary for downsizing among certain femoral components. Where posterior chamfer 18 remains sufficiently large after recutting of posterior cut 14, smaller provisional component 120 and/or smaller permanent component 170 may simply have a shorter posterior chamfer surface 38 to accommodate the non-recut posterior chamfer 18. Thus, within certain ranges of component sizes, only a single additional resection may be needed to facilitate the effective use of the next-smallest component size.

Thus, any of a wide range of components from smallest component 180 to largest component 200 may be mounted to femur 2 by altering only two of the five initial cuts made to prepare femur 2 for receipt of a relatively smaller orthopaedic femoral implant component. Advantageously this large range and high resolution of potential component choices offers a high degree of intraoperative flexibility when implanting prosthetic components.

In FIG. 7B, pegs 189, 199, 209 are provided for fixation of components 180, 190, 200 to femur 3. Although pegs 189, 199, 209 are shown in different locations, it is contemplated that these pegs may be in a common location, similarly to pegs 72, 172 of femoral components 70, 170 respectively. As noted above, disposing pegs 189, 199, 209 at a common anteroposterior location allows a peg hole to be drilled into distal cut 12 during the initial resection.

3. Adaptation of the Implant System for Anterior and Distal Recutting

The system of provisional components illustrated in FIGS. 2A-6B includes posteriorly disposed cut slots for altering posterior cuts 14, 18 (FIG. 1B). As noted above, these cut slots allow a smaller provisional component to be implanted upon femur F, particularly a component with a smaller posterior condylar compartment. Thus, the above-mentioned embodiment is particularly useful for downsizing to a femoral component that is smaller in the posterior compartment. Because the posterior portion of femoral condyles interact with the tibia in flexion, downsizing to a smaller posterior compartment can be used to reduce ligament tension in flexion.

However, alternative embodiments may be provided which operate to downsize the distal and anterior compartments, as described below.

Figure 8:
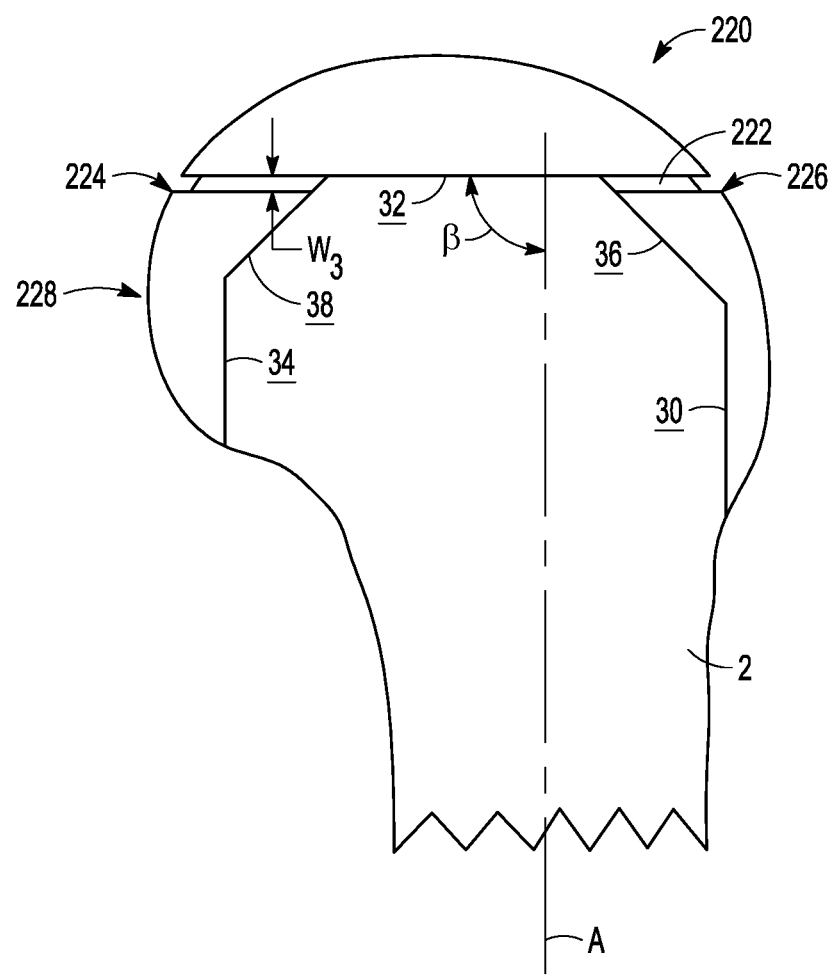
FIG. 8 is a side elevation view of the distal femur shown in FIG. 1A, shown with an initial larger provisional orthopaedic implant with integral cutting guide adapted for a distal recut in accordance with the present disclosure.

In one such alternative embodiment, provisional femoral components in accordance with the present disclosure may include distally disposed cut slots for altering distal cut 12, such as for altering the articular characteristics of a knee prosthesis in an extension orientation. Referring to FIG. 8, provisional component 220 includes medial distal cut slot 222 and a corresponding lateral distal cut slot (not shown), with the lateral slot a substantially identical mirror image (about a sagittal plane) of medial distal cut slot 222.

Except as otherwise specified herein, provisional component 220 is similar to provisional component 20, described above. For example, provisional component 220 includes surfaces 30, 32, 34, 36, 38 adapted to cooperate with cuts 10, 12, 14, 16, 18 of femur 2 (FIGS. 1A and 1B). However, distal cut slot 222 has a distal location and is oriented to extend generally anteroposteriorly from posterior portion 224 of component 220 to anterior portion 226 thereof. Distal cut slot 222 is provided in lieu of posteriorly disposed cut slots as described above, though it is contemplated that distal cut slot 222 can be included in provisional components which also include posterior cut slots.

Cut slot 222 extends into component 220 from lateral to medial without extending entirely through medial condyle 228. However, similar to cut slots 40, 42, distal cut slot 222 may also extend from the intercondylar fossa (not shown) outwardly in a medial direction. Distal cut slot 222 defines width $W_3$, which corresponds to a desired amount of bone resection at distal cut 12 in a similar manner to the correspondence between $W_1$ and $W_2$ and bone resection amounts for posterior cut 14 and posterior chamfer 18 as described above.

Cut slot 222 and the mirror-image lateral distal cut slot (not shown) are used in a similar manner as posterior cut slots 40, 42, 56, 58 discussed above. However, use of distal cut slot 222 reduces the overall longitudinal extent of femur 2, rather than the overall anteroposterior resection distances $D_1$, $D_2$ (FIGS. 2B and 4). Thus, instead of reducing ligament tension in flexion while maintaining tension in extension, as occurs when posterior cut and posterior chamfer are further resected as discussed above, ligament tension in extension is reduced by the further resection of distal cut 12 while maintaining tension in flexion.

In use, for example, a surgeon may find that using provisional component 220 results in optimal tissue balance in flexion but a higher-than-optimal tension in extension. Medial distal cut slot 222 (and the corresponding lateral cut slot) may then be employed to further resect femur 2, thereby preparing femur 2 to receive a relatively more proximally located femoral component. This more-proximal prosthetic component reduces the tension in extension while retaining the previously-observed optimal tension in flexion.

When the surgeon is satisfied with the revised ligament tension in extension, a femoral finishing guide (not shown) may be attached to the distal portion of femur 2 to revise anterior cut surface 30, anterior chamfer cut surface 36, posterior cut surface 34 and posterior chamfer cut surface 38, in accordance with commonly accepted methods. Provisional component 220 is then re-installed onto femur 2 and once again checked for optimal ligament tension in flexion and extension, with the extension tension now reduced due to the additional distal cuts performed using slots 222, 224. Distal recut slots 222, 224 may be used to further resect distal surface 32 of femur 2 if tension in extension is still higher than optimal, or a permanent component corresponding to provisional component 220 may be installed if extension and flexion ligament tension is found to be optimal after recutting (as discussed above with respect to other trial component embodiments).

Depending on which particular angle (or angular range) of flexion the surgeon desires to alter with recutting, the angle of distal recut slot 222 may be changed. Referring still to FIG. 8, provisional component 220 defines angle 3 in a generally sagittal plane. Angle β is the angle between femoral axis A and distal cut slot 222 (in the illustrated embodiment, distal surface 32 is the distal terminus of cut slot 222). Where angle 1 is about 90 degrees, i.e., femoral axis A is generally perpendicular to cut slot 222, ligament tension in a full extension knee orientation will be primarily affected by recutting. As cut slot 222 cants proximally-posteriorly, i.e., toward the angle of posterior chamfer surface 38, ligament tension will be affected in deeper flexion orientations.

It is also contemplated that angle β may be changed by a recutting process as described herein. Distal recut slot 222 may define an angle 1 that is different from the angle defined by the initial distal cut 12, such that when saw blade 60 is passed into cut slot 222, a new distal cut 12 is defined having a new and different angle with respect to axis A. With the new distal cut 12 defined, the surgeon may revise the other cuts 10, 14, 16, 18 using any suitable methods and apparatuses, such as a femoral finishing guide as described herein. Moreover, it is contemplated that any of guides 20, 120, 220 and 320 may be used to alter the angle of the corresponding cut using a cut slot which defines a new angle.

Figure 9:
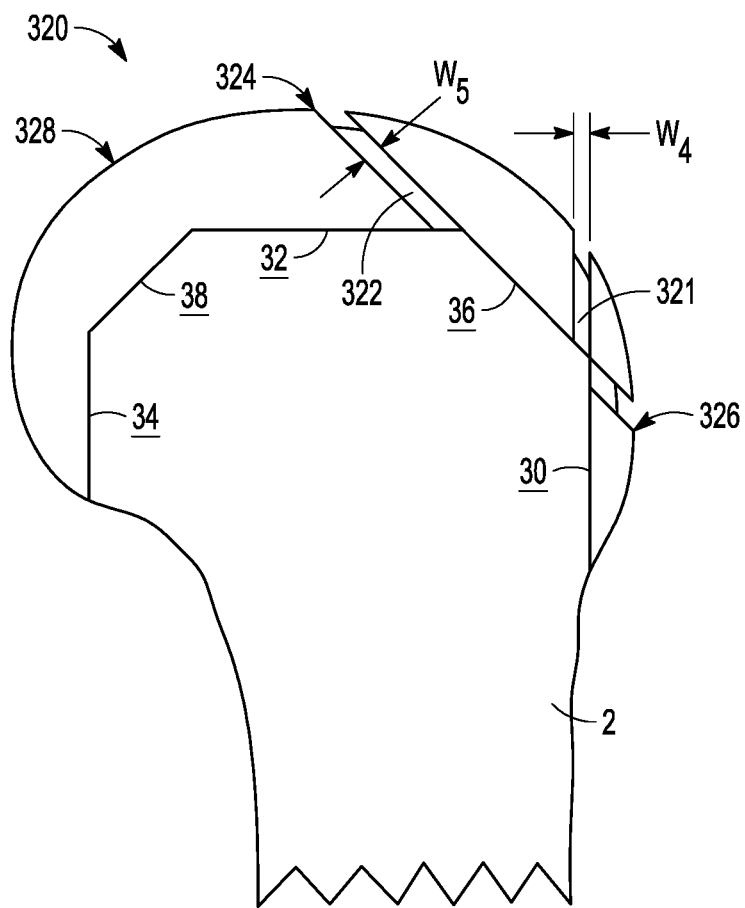
FIG. 9 is a side elevation view of the distal femur shown in FIG. 1A, shown with an initial larger provisional orthopaedic implant with integral cutting guide adapted for anterior and anterior chamfer recuts in accordance with the present disclosure.

In still another alternative embodiment, it is contemplated that provisional femoral components in accordance with the present disclosure may include anteriorly disposed cut slots for altering anterior cut 10 and/or anterior chamfer 16 (FIGS. 1A and 1B), such as for optimizing patellar interaction or to avoid notching femur 2 with the femoral component. Referring to FIG. 9, provisional component 320 includes medial anterior cut slot 321 and medial anterior chamfer cut slot 322, with corresponding lateral anterior and anterior chamfer cut slots (not shown). The lateral anterior and anterior chamfer cut slots are substantially identical mirror images of medial anterior and anterior chamfer cut slots 321, 322, respectively, about a sagittal plane.

Except as specified herein, provisional component 320 is similar to provisional component 20, described above. For example, provisional component 320 includes surfaces 30, 32, 34, 36, 38 adapted to cooperate with cuts 10, 12, 14, 16, 18 of femur 2 (FIGS. 1A and 1B). However, anterior cut slot 321 has an anterior location and is oriented to extend in a generally proximal-distal direction, i.e., along a direction parallel to the plane defined by anterior surface 10 of femur 2. Anterior chamfer cut slot 322 extends from distal portion 324 of medial condyle 328 to anterior flange 326 of component 320. Anterior cut slots 321, 322 are provided in lieu of posteriorly and/or distally disposed cut slots as described above, though it is contemplated that anterior cut slots 321, 322 can be included in provisional components which also include posterior and/or distal cut slots.

Similarly to cut slots 40, 42, anterior cut slots 321, 322 may extend from lateral to medial without extending entirely through medial condyle 328, or may extend from the intercondylar fossa (not shown) outwardly in a medial direction. Anterior cut slots 321, 322 define widths $W_4$ and $W_5$, respectively, which correspond to a desired amount of bone resection at anterior cut 10 and anterior chamfer cut 16 (FIGS. 1A and 1B) in a similar manner to the correspondence between $W_1$ and $W_2$ and bone resection amounts for posterior cut 14 and posterior chamfer 18.

Cut slots 321, 322 (and the mirror-image lateral anterior cut slots) are used in a similar manner as posterior cut slots 40, 42, 56, 58 discussed above. However, use of anterior cut slots reduces the overall anteroposterior resection distances (i.e., $D_1$ and $D_2$ described above) at anterior cut 10 rather than posterior cut 14. Thus, instead of reducing ligament tension in flexion, as occurs when posterior cut and posterior chamfer are further resected as discussed above, interaction between the patella and femoral component 320 is affected.

A kit of components may be provided to fit femurs with ever-more resected anterior cuts 10. The components of this kit can be aligned with posterior surfaces (analogous to posterior surface 34 of component 20) and posterior chamfer surfaces (analogous to posterior chamfer surface 38 of component 20) are designed to align with one another, while the anterior chamfers (analogous to anterior chamfer surface 36 of component 20) change length as anterior surfaces (analogous to anterior surface 30 of component 20) are spaced ever farther from one another.

In use, for example, a surgeon may find that provisional component 320 provides optimal balance in both flexion and extension, but may be suboptimal in another way, e.g., higher-than-optimal tension between the patella and anterior flange 326, limited range of motion, etc. Medial anterior cut slot 321 and anterior chamfer cut slot 322 (and the corresponding lateral cut slots) may then be employed to further resect femur 2, thereby preparing femur 2 to receive a femoral component with a relatively more posteriorly located patellar flange.

The more-posterior patellar flange reduces the tension between anterior flange 326 and the adjacent patella, while retaining the optimal flexion and extension tension. Because posterior surface 34 of component 320 is then spaced from posterior surface 14 of femur 2 by an amount equal to cut width $W_4$, an augment (not shown) having equal width may be placed therebetween to reestablish firm and complete contact between component 320 and femur 2. Alternatively, a relatively smaller femoral component may be provided which fits femur 2 after anterior recutting, in similar fashion to smaller femoral component 170 described above.

Advantageously, use of femoral cut guides made in accordance with the present disclosure constrains saw blade 60 within the respective cut slots during the resection process. This, in turn, promotes clean, controlled resection of the bone, even where only a thin margin of bone is being removed as in the case of downsizing. This high level of blade control minimizes the chance that a surgeon will unintentionally create a notch or other stress riser in the bone, e.g., from vibration of saw blade 60.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A knee prosthesis system comprising:
   a first provisional component having a first articular surface and a first bone contacting surface disposed opposite the first articular surface, the first bone contacting surface comprising:
   a first anterior surface defining a first, generally coronal anterior plane;
   a first distal surface defining a first, generally transverse plane; and
   a first posterior surface defining a first, generally coronal posterior plane, a first distance extending anteroposteriorly from said first posterior plane to said first anterior plane,
   said first provisional component further comprising a posterior cut slot defining a posterior cut width and adapted to receive a cutting instrument;
   a second component having a second articular surface defining a second articular surface geometry and a second bone contacting surface disposed opposite the second articular surface, the second bone contacting surface comprising:
   a second anterior surface defining a second, generally coronal anterior plane;
   a second distal surface defining a second, generally transverse plane; and
   a second posterior surface in a second, generally coronal posterior plane, a second distance extending anteroposteriorly from said second posterior plane to said second anterior plane; and
   said second distance less than said first distance by an amount equal to said posterior cut width.

2. The knee prosthesis system of claim 1, wherein said posterior cut width is equal to a width of said posterior cut slot.

3. The knee prosthesis system of claim 2, wherein said width of said posterior cut slot is measured anteroposteriorly from said first posterior surface of said first provisional component.

4. The knee prosthesis system of claim 1, wherein:
   said first bone contacting surface of said first provisional component further includes a first posterior chamfer surface extending between said first posterior surface and said first distal surface,
   said first provisional component further comprising a posterior chamfer cut slot defining a posterior chamfer cut width and adapted to receive the cutting instrument; and
   said second bone contacting surface of said second component further includes a second posterior chamfer surface extending between said second posterior surface and said second distal surface,
   said second posterior chamfer surface is inset along a line normal to said first posterior chamfer surface by a distance equal to said posterior chamfer cut width, as measured when said first and second anterior surfaces are aligned and said first and second distal surfaces are aligned.

5. The knee prosthesis system of claim 4, wherein said posterior chamfer cut width is equal to a width of said posterior chamfer cut slot.

6. The knee prosthesis system of claim 4, wherein said posterior chamfer cut slot of said first provisional component defines a cut slot surface positioned to be coplanar with a posterior chamfer surface of a resected femur when said first provisional component is mounted to the femur.

7. The knee prosthesis system of claim 4, wherein said second component comprises a second provisional component, said second provisional component comprising:

a second posterior cut slot defining a second posterior cut width; and a second posterior chamfer cut slot defining a second posterior chamfer cut width, said second posterior cut slot and said second posterior chamfer cut slot each adapted to receive the cutting instrument.

8. The knee prosthesis system of claim 7, wherein said posterior cut width of said first provisional component is equal to said second posterior cut width.

9. The knee prosthesis system of claim 7, wherein said posterior chamfer cut width of said first provisional component is equal to said second posterior chamfer cut width.

10. The knee prosthesis system of claim 1, wherein:

said first bone contacting surface of said first provisional component further includes a first anterior chamfer surface extending between said first anterior surface and said first distal surface, said first anterior chamfer surface defining a first angle with respect to said first anterior surface; and said second bone contacting surface of said second component further includes a second anterior chamfer surface extending between said second anterior surface and said second distal surface, said second anterior chamfer surface defining a second angle with said second anterior surface, said first angle substantially equal to said second angle.

11. The knee prosthesis system of claim 10, wherein said first anterior chamfer surface defines a first sagittal extent, and said second anterior chamfer surface defines a second sagittal extent, said first and second sagittal extents being within about 1 mm of one another.

12. The knee prosthesis system of claim 10, wherein said first anterior chamfer surface of the first provisional component defines a first anterior chamfer surface profile in a sagittal plane, said second anterior chamfer surface of the second component defines a second anterior chamfer surface profile in the sagittal plane, said first anterior chamfer surface profile being substantially the same as said second anterior chamfer surface profile.

13. The knee prosthesis system of claim 1, wherein said second component comprises one of a provisional component and a permanent component.

14. The knee prosthesis system of claim 1, wherein:

said first provisional component comprises a first peg hole drill guide, said second component comprising a second provisional component including a second peg hole drill guide, said first and second peg hole drill guides being substantially coaxial when said first and second provisional components are aligned in a sagittal plane.

\* \* \* \* \*